United States Patent

Galchenkov et al.

[19]

[11] Patent Number: 6,167,299

[45] Date of Patent: Dec. 26, 2000

[54] METHOD FOR RECORDING SKIN GALVANIC REACTIONS AND DEVICE FOR REALIZING THE SAME

[75] Inventors: Leonid Arkad'evich Galchenkov; Valery Vasiljevich Dementienko; Lidyja Georgievna Koreneva; Andrey Genrikhovich Markov; Vjacheslav Markovich Shakhnarovich, all of Moscow, Russian Federation

[73] Assignee: Zakrytoe Aktsionernoe Obschestvo "Neurocom", Moscow, Russian Federation

[21] Appl. No.: 09/194,352

[22] PCT Filed: May 22, 1997

[86] PCT No.: PCT/RU97/00162

§ 371 Date: Apr. 23, 1999

§ 102(e) Date: Apr. 23, 1999

[87] PCT Pub. No.: WO97/45162

PCT Pub. Date: Dec. 4, 1997

[30] Foreign Application Priority Data

Mar. 28, 1996 [RU] Russian Federation ............ 96-110526

[51] Int. Cl.⁷ ...................................................... A61B 5/05
[52] U.S. Cl. ............................................................ 600/547
[58] Field of Search ...................................... 600/346, 547

[56] References Cited

U.S. PATENT DOCUMENTS

| | | | |
|---|---|---|---|
| 4,088,125 | 5/1978 | Forgione et al. | 600/547 |
| 4,450,527 | 5/1984 | Sramek | 600/547 |
| 4,595,018 | 6/1986 | Rantala . | |

FOREIGN PATENT DOCUMENTS

| | | |
|---|---|---|
| 1217340 | 3/1986 | Russian Federation . |
| 1286160 A1 | 1/1987 | Russian Federation . |
| 1421299 A1 | 9/1988 | Russian Federation . |
| 1489720 A1 | 6/1989 | Russian Federation . |

OTHER PUBLICATIONS

A.A. Aldersons, *Mechanisms of Electrodermal Reactions*, Riga, "Zinatine," 1985, pp. 59–63.

*Primary Examiner*—William E. Kamm
*Attorney, Agent, or Firm*—McEachran, Jambor, Keating, Bock & Kurtz

[57] ABSTRACT

In the field of medicine and medical engineering, in particular to methods and devices for diagnostics of the status of an alive organism basing on skin electrical conductivity, a method and device for monitoring galvanic skin reactions is usable in experimental and clinical medicine, as well as in psychophysiology, pedagogics and sports medicine. The device enables to eliminate interference caused by artifacts of a subject's movements as well as interference brought about by non-biological causes (various electrical noises and equipment drift). The method is featured by the fact that the shape of each pulse of the sequence of pulses is being analyzed in the phasic component frequency band. For this purpose monitored are the first and the second derivatives in time of the logarithm of skin electric conductivity. The value of the trend brought about by the tonic component is determined, and the value of the first derivative is adjusted through subtraction of the trend value from it. Further, the time of the onset of the first derivative pulse is determined as the moment of the second derivative exceeding a threshold value, and then the shape of said pulse is analyzed. The analysis of the pulse shape could be carried out either by hardware or by software method. Should the parameters of this shape meet certain preset criteria, the analyzed pulse is classified as a pulse of the phasic component, otherwise it is put down to artifacts. Two devices for galvanic skin reaction monitoring are described.

14 Claims, 4 Drawing Sheets

METHOD FOR RECORDING SKIN GALVANIC REACTIONS AND DEVICE FOR REALIZING THE SAME

BACKGROUND OF THE INVENTION

1. Field of the Invention

The invention relates to the field of medicine and medical engineering, in particular to methods and devices for diagnostics of the status of an alive organism basing on skin electrical conductivity and can be used in experimental and clinical medicine, as well as in psychophysiology, pedagogics and sports medicine.

2. Background Art

It is known that electrical conductivity of the skin of an alive organism is a sensitive indicator of its physiological and psychological state, parameters of the conductivity response onto an external influence, the so-called galvanic skin reaction (hereinafter referred to as GSR) being capable of estimating the psychophysiological status of an individual. In GSR studies, a tonic and a phasic components of electrodermal activity (hereinafter referred to as EDA) can be distinguished. Changes of tonic activity features in skin conductivity occur rather slowly, with characteristic times of several minutes and more. Phasic activity is implemented in processes occurring much faster on the background of tonic activity, its characteristic times being of the order of few seconds. It is the phasic activity that basically characterizes the response of an organism to an external stimulus, and this is referred to in the technical and patent literature as GSR.

The known methods of GSR monitoring include imposing on an subject's skin of a pair of electrodes connected to a source of a probing current and a monitoring device for the current in the circuit comprising electrodes and the source of current. The response occurs when sweat glands excrete a secret and momentary pulses of electrical current arise in the circuit. Such pulses are generated either spontaneously, or owing to stress or another stimulus (A. A. Aldersons, Mechanisms of Electrodermal Reactions, Riga, "Zinatne", 1985, pp. 59–63).

The known devices for GSR monitoring include a source of electric current connected to electrodes, an electric signal monitoring unit, and a signal processing unit. The signal processing consists in detection of the phasic component of EDA on the background of EDA tonic component. This can be embodied, for example, in the unit using a bridge circuit and a series of direct-current amplifiers with individual zero setting. The value of the tonic component (hereinafter referred to as the trend) is calculated by an analog method, and this is further subtracted from the signal. This value is also used to adjust the base line of graph plotter to zero (U.S. Pat. No. 4,331,160, ZITO, 1982).

In another known device (SU, A1, 1725829, Institute of General Judicial Psychiatry., 1992) the comparative level of the phasic component of the EDA with respect to the trend is determined by a circuit comprising highpass and lowpass filters at the outputs of respective amplifiers, as well as a dividing circuit.

One should mention that in the abovementioned methods and devices for galvanic skin reaction monitoring there are no means provided for the analysis of the EDA phasic component pulses, these pulses being capable of fetching the additional information on a status of the subject.

Closest to the method claimed is the method of monitoring of galvanic skin reaction implemented in the device (SU, A1, 1567427, Moscow Institute of Railway Transport Engineers., 1990). The method requires fastening two electrodes on the body of a subject, application of an electrical voltage to these, monitoring of time variation of the electric current flowing between electrodes and monitoring of the current pulses in the frequency band peculiar to phasic component of EDA.

The prototype of the device for galvanic skin reactions monitoring is the device implementing the above method (SU, A1, 1567427). This device comprises electrodes with a means of their fastening to the skin these electrodes being connected to the input unit, a means for signal discrimination in frequency bands of phasic and tonic components of EDA, a means for detecting EDA phasic component pulses, a means for suppression of pulse interference, and a monitoring unit.

However, the abovementioned method and device are not free from interference brought about by the subject's motions (artifacts) superimposed onto GSR signals temporal sequence and similar to pulses of the EDA phasic component. These artifacts could be, for example, brought about by uncontrollable movements of the subject in the course of registration (so-called artifacts of movement). In a signal there can also exist noises due to variation of contact resistance between electrodes and the person's skin. The abovementioned interference, including artifacts of movement, can feature characteristic frequencies comparable to those of a phasic component of EDA, which makes their revealing and consideration a distinct problem. Heretofore, this problem was being solved by installation onto the body of a subject of special gauges, in addition to electrodermal ones, which complicated experiments (R.NICULA.—"Psychological Correlates of Nonspecific SCR", —Psychophysiology; 1991, vol.28, No 1, p.p. 86–90). Besides, the trend features minimum characteristic time of change of the order of several minutes. These variations should be accounted for especially in cases when amplitude and frequency of the EDA phasic component are rather small, whereas tonic changes are highest. Such kind of a process is also characteristic for hardware drift of the measuring circuit, and it can be wrongly interpreted as an information signal.

SUMMARY OF THE INVENTION

An object of the present invention is development of a method of GSR monitoring and of a device for its implementation free from interference caused by artifacts of a person's movements as well as from interference brought about by non-biological causes (technogenic and atmospheric electrical discharges and equipment drift). This object is achieved without employment of any additional devices similar to those described in the abovementioned work of R.NICULA. The information on interference is extracted directly from the GSR signal, and the claimed technique relies upon the detailed analysis of the shape of each electrical pulse of the sequence of pulses arriving from electrodes. The pulse of the EDA phasic component is known to be a spontaneous momentary increase in skin conductivity followed by the subsequent return to the initial level. Such a pulse possesses a specific asymmetry in the shape, namely, a steep leading edge and a more soft-sloped trailing edge (see "Principles of Psychophysiology. Physical, Social, And Inferential Elements".—Ed. John T. Cacioppo and Louis G. Tassinary.—Cambridge University Press, 1990, p.305). To determine the required parameters of this GSR pulse, differentiation of the input signal logarithm is performed (for example, by means of an analog differentiation).

The method of the present invention includes fastening of two electrodes on the body of a subject, feeding of the dc electric voltage to said electrodes, monitoring of time variation of the electrical current flowing between these electrodes and monitoring of electric current pulses in the frequency band of the phasic component of EDA.

The improvement brought about by the claimed method consists in analyzing of the shape of each pulse in the sequence of pulses of electric current in the frequency band of phasic component of EDA. For this purpose the signal is recorded as the time derivative of the logarithm of electric current numerical value; further, the value of the trend brought about by signal variation in the frequency band of tonic component of EDA, is determined; and the value of the first derivative is adjusted through subtraction of the trend value from it. Further, the second derivative in time of the logarithm of electric current numerical value is determined, the onset of said signal pulse being determined as the moment of said second derivative exceeding a threshold value, and then conformity of the pulse shape to certain preset criteria is verified. Should this conformity exist, the analyzed pulse is classified as a pulse of the EDA phasic component, in case of lack of such conformity the pulse is put down to artifacts.

The trend value could be determined as the first derivative average over the time interval characteristic for the tonic component, basically 30 to 120 sec. Besides, the trend value could be determined as the first derivative average over the time interval 1 to 2 sec., provided first and second derivative values being less than certain preset threshold values over this time interval.

The onset of the first derivative pulse could be considered the moment when the second derivative exceeds the threshold value by at least 0.2%.

In determining the pulse shape, it is expedient to register the maximum ($f_{MAX}$) and the minimum ($f_{MIN}$) values of the first time derivative minus the trend value, their ratio r, and the time interval ($t_x$) between the minimum and the maximum of the first derivative. The moments of the first derivative achieving its maximum and minimum values are determined as the moments of the second derivative sign change.

The criteria of the analyzed pulse belonging to EDA phasic component signal could be the following inequalities (for the filtered signal):

$0.5 < f_{MAX} < 10$ $-2 < f_{MIN} < -0.1$  (*)

$1.8 < t_x < 7$ $1.5 < r < 10$

The above attributes of the claimed method essential for achievement of the object of the invention provide for achievement of the technological result, namely, enhancing of an electronic interference immunity in galvanic skin reaction monitoring in conditions of real interference of various origins and artifacts of movement of the subject himself. The means for implementation of the present method described hereinafter can be embodied via either hardware or software, their essence being clarified from the description given below.

The device for monitoring of GSR comprises an input unit with electrodes connected to it and a means for their fastening to a subject's body, a means for suppression of pulse interference, a means for discrimination of signals in frequency bands of phasic component of EDA, a means for detecting pulses of phasic component of EDA, and a monitoring unit. With this, the improvement consists in the assembly comprising the means for signal discrimination in the frequency band of EDA phasic component and the means for detection of pulses of said component being embodied as the assembly comprising a unit for conversion of the logarithm of the input signal into the first and the second derivatives in time and a pulse shape analysis unit. Besides, the unit for conversion of the logarithm of the input signal into the first and the second derivatives in time and the pulse shape analysis unit are connected serially to the input unit, the output of the pulse shape analysis unit being connected to the monitoring unit input.

The device can be embodied in such a way that the assembly comprising the means for suppression of pulse interference, the means for signal discrimination in the frequency band of EDA phasic component and the means for detection of pulses of said component is embodied as an assembly comprising a lowpass filter, a unit for conversion of the logarithm of the input signal into the first and the second derivatives in time, and a pulse shape analysis unit.

The input unit could comprise a stabilized dc electric voltage source and a resistor connected in series to electrodes, a logarithmic amplifier with a differential input stage, the resistor shunting the logarithmic amplifier inputs.

The unit for conversion of the logarithm of the input signal into the first and the second derivatives in time could be embodied as a first and a second differentiators and a second lowpass filter, the output of the first differentiator being connected to the input of the second differentiator and of the second lowpass filter, outputs of the latters being the outputs of the unit for conversion of the logarithm of the input signal into the first and the second derivatives in time.

The shape analysis unit can include a means for determination of the maximum conductivity variation rate at leading and trailing edges of the pulse being analyzed, a means for evaluation of its shape asymmetry, a means for determination of pulse width, a means for comparison of said values with the preset limits for generation of the signal indicating belonging of the pulse being analyzed to EDA phasic component.

As a version of implementation of the method, suggested is a GSR monitoring computer-based device which performs digital signal processing. Such a device comprises an input unit with electrodes connected to it and a means for their fastening to a subject's body and a computer. The input unit comprises a stabilized dc electric voltage source, a resistor, an amplifier with a differential input stage, an analog-to-digital converter. With this, the stabilized dc electric voltage source is connected in series to the resistor and the electrodes, said resistor shunting the inputs of said amplifier, the output of which is connected to the input of the analog-to-digital converter, the digital output of which being connected to the digital input of the computer. In this device, suppression of pulse interference, discrimination of signals in frequency bands of phasic component of EDA, detecting pulses of phasic component of EDA, and monitoring of said pulses are implemented as a computer program.

According to the information available to the inventors, the technological result, i.e. enhancement of reliability in discrimination of EDA phasic component pulses does not follow obviously from the prior art information. The inventors claim not knowing any sources of the information disclosing the employed technique of signal shape analysis enabling one to discriminate the valid EDA phasic component pulses from artifacts, including those caused by movements of the subject. The above allows one to consider the invention satisfying the condition of the invention idea being not obvious.

BRIEF DESCRIPTION OF THE DRAWINGS

Hereinafter the invention is explained in relation to the following description, by way of examples, not limiting the present invention and taken in conjunction with the accompanying drawings wherein.

EXAMPLES OF THE INVENTION EMBODIMENTS

The claimed method of GSR monitoring will become more apparent when, by way of example, operation of devices for its implementation is explained.

Figure 1:
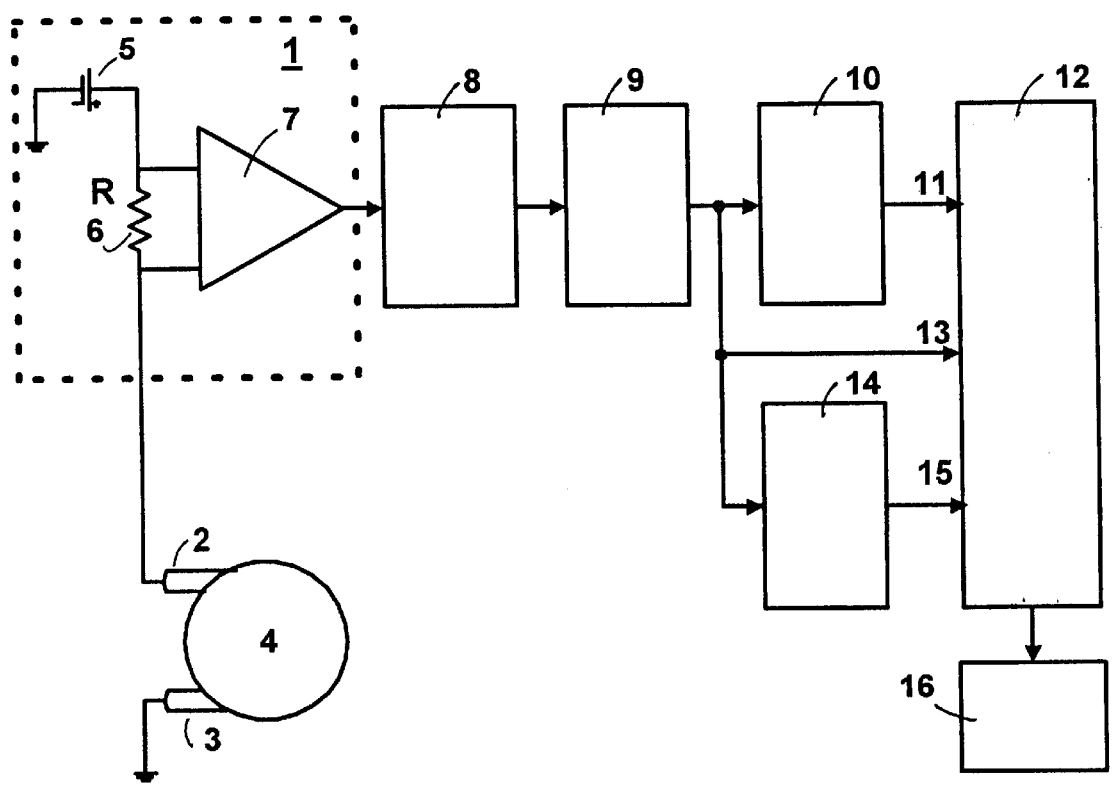
FIG. 1 is the flowchart of the device for galvanic skin reactions monitoring in compliance with the present invention.

The device for GSR monitoring (FIG. 1) includes the input unit 1 connected to the electrodes 2, 3 for application onto the skin of the subject 4. The electrodes may be embodied in various versions, for example as two rings, a wrist bracelet and a ring, a bracelet with two electrical contacts. The only requirement to these is that the electrodes should provide a stable electrical contact with the subject skin. The electrodes 2, 3 are connected to the stabilized voltage source 5 through the resistor R (6), said resistor being connected to the input of the differential logarithmic amplifier 7, the output of which is the output of the input unit 1, and is connected to the means for pulse interference suppression 8, for example, to the input of one or more lowpass filters connected serially. In this example, a single filter 8 is employed, the output of which is connected to the input of the first differentiator 9. The output of the first differentiator 9 is connected to the input of the second differentiator 10, the output of which is connected to the input 11 of pulse shape analyzer unit 12. Besides, the output of the first differentiator 9 is connected directly to the unit 12 through the input 13, and to the other input 15 of pulse shape analyzer unit 12 through the second lowpass filter 14. The signal from the output of said second lowpass filter 14 is used in the unit 12 for compensation of EDA tonic component. The cut-off frequency of the lowpass filter 8 constitutes ca.1 Hz, and the cut-off frequency of the second lowpass filter 14—about 0.03 Hz, which corresponds to higher limits of frequency bands of EDA phasic and tonic components. The output of the pulse shape analyzer unit 12 is connected to the monitoring unit 16.

The analysis of shape of the EDA phasic component pulses providing for their discrimination from artifacts of movement and from other interferences is carried out employing characteristic parameters of the signal, the latters further being compared to allowable limits. These characteristic parameters include:

Maximum slope of leading and trailing edges of the pulse; this can be expressed as the maximum ($f_{MAX}$) and minimum ($f_{MIN}$) values of the first derivative of the input signal (minus the trend) logarithm;

Width $t_x$ of the pulse determined as the time interval between the moments of achieving by the first derivative of its maximum and minimum values;

Ratio of absolute values of the first derivative (minus a trend) in the maximum and the minimum: $r=(f_{MAX})|/|(f_{MIN})|$. This value r is a measure of the analyzed pulse asymmetry.

Thus, the conditions for the analyzed pulse classification as a pulse of EDA phasic component rather than artifacts of movement and interference, are the limits:

$$m_1 < f_{MAX} < m_2;$$
$$m_3 < f_{MIN} < m_4; \quad\quad (*)$$
$$r_1 < r < r_2;$$
$$t_1 < t_x < t_2;$$

Where:

$m_1$, $m_2$ are minimum and maximum allowable values of the first derivative (minus the trend) at the maximum, %/s;

$m_3$, $m_4$ are minimum and maximum allowable values of the first derivative (minus the trend) at the minimum, %/s;

$t_1$, $t_2$ are minimum and maximum time intervals between extrema of the first derivative, s;

$r_1$, $r_2$ are minimum and maximum values of the ratio r.

These limits have been shown to vary both from one subject to another, and for the same subject for different measurements. At the same time, statistical processing of research results has shown that 80 to 90 percent of signals are actually GSR signals, provided the following values for the limits are used: $m_1=0.5$, $m_2=10$, $m_3=-2$, $m_4=-0.1$, $t_1=1.8$, $t_2=7$, $r_1=1.5$, $r_2=10$.

Figure 2:
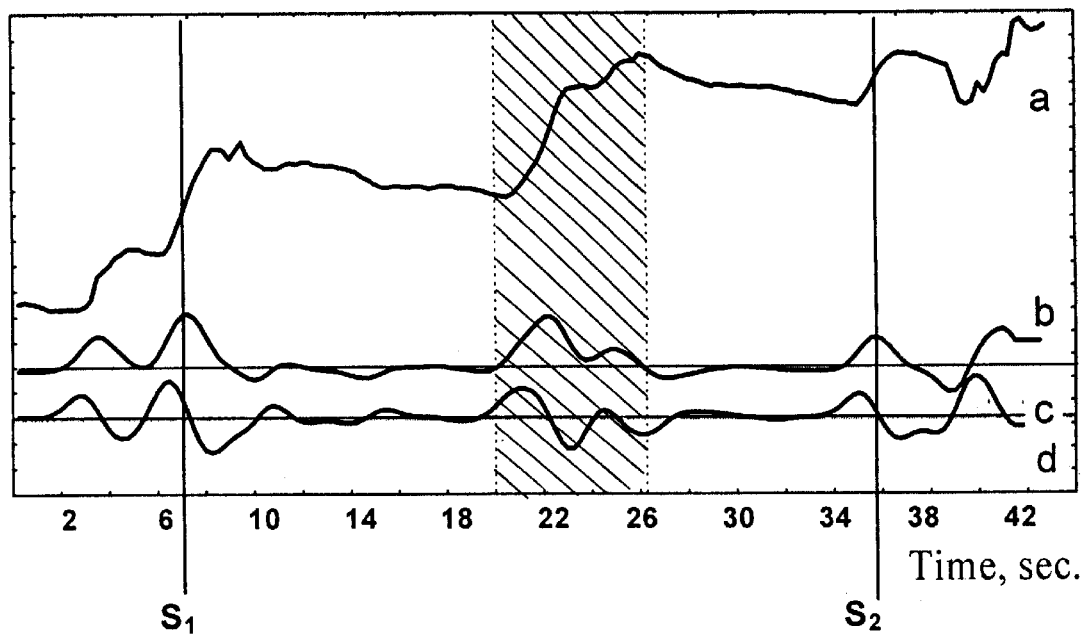
FIG. 2 shows the real example of the initial signal (a) shape and the results of its processing by the device under the invention (b, c, d)

FIG. 2 shows the example of processing of a real GSR signal.

Plot (a) demonstrates the shape of the signal—U=100. In ($I_{meas}$) at the output of the logarithmic amplifier 7, plots (b) and (c)— the first (U') and the second (U") derivatives of the plot (a) signal. As the circuit takes the logarithm of the signal, after differentiation in elements 9 and 10 the numerical values of the signal derivatives U' and U" are in units % Is and %/s², respectively.

The plot (d) on the same FIG. 2 is the result of GSR signal discrimination from the background of the trend and of interference carried out in compliance with the present invention. The labels $S_1$ and $S_2$ denote signals corresponding to the time of phasic component pulses occurrence. One should emphasize the experimental fact that the pulse apparently similar to those marked with labels $S_1$ and $S_2$ in the time interval 20 to 26 sec. (the shaded area) is the interference. Verification of pulse shape conformity with the specified four criteria (*) is performed by the pulse shape analysis unit 12.

The trend value can be defined as an average value of the first derivative over the time interval characteristic for the tonic component, basically 30 to 120 s. Besides, the trend value can be defined as an average value of the first derivative over the time interval 1 to 2 s, provided the values of the first and the second derivatives are less than the given threshold values during this interval of time. In the second variant the trend is determined more accurately, however in case of abundance of interference the abovementioned conditions can be not valid for a long time period. In this case the trend should be calculated by the first method.

Figure 3:
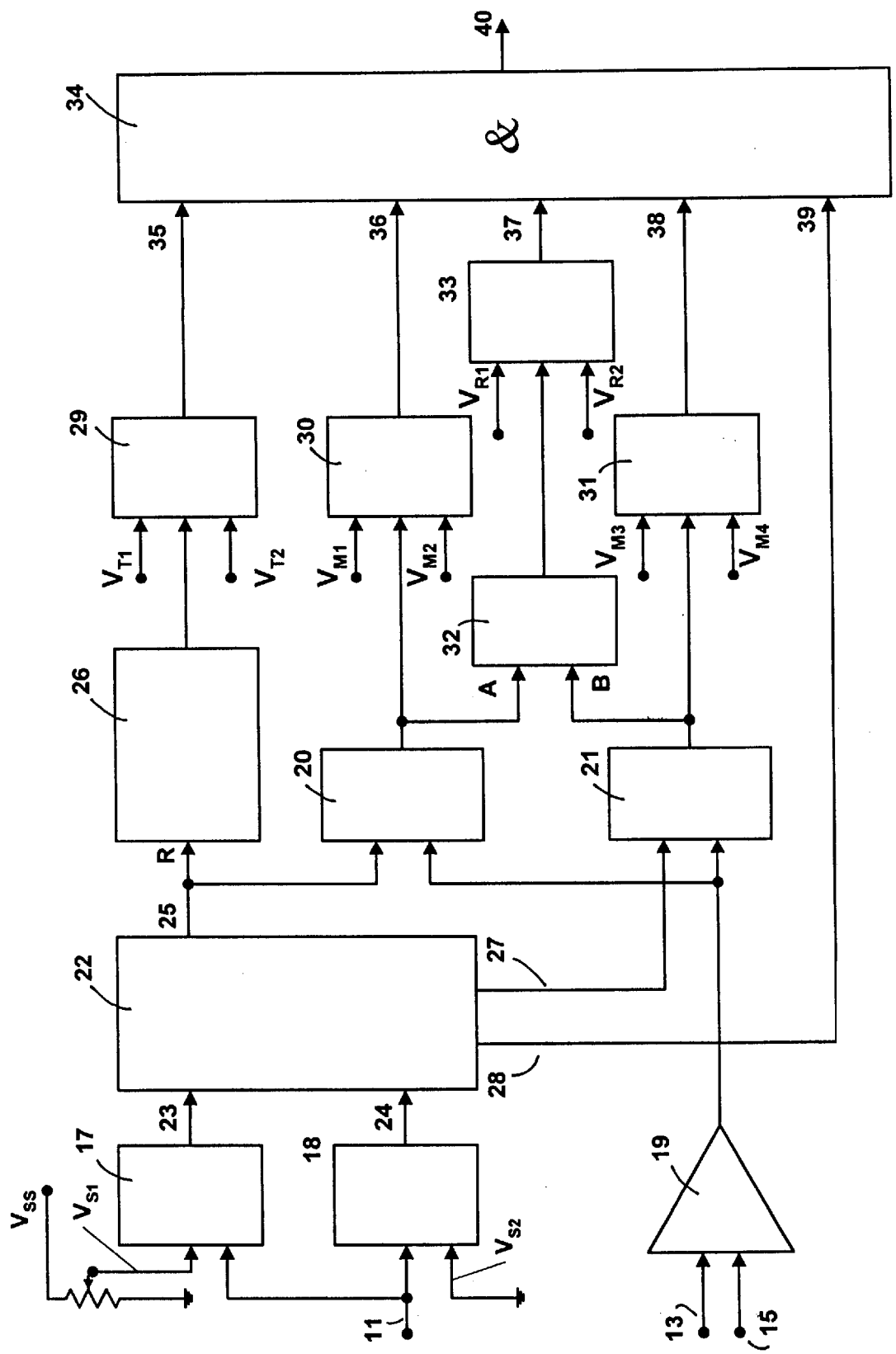
FIG. 3 is the hardware implementation of the pulse shape analysis unit.
Figure 4:
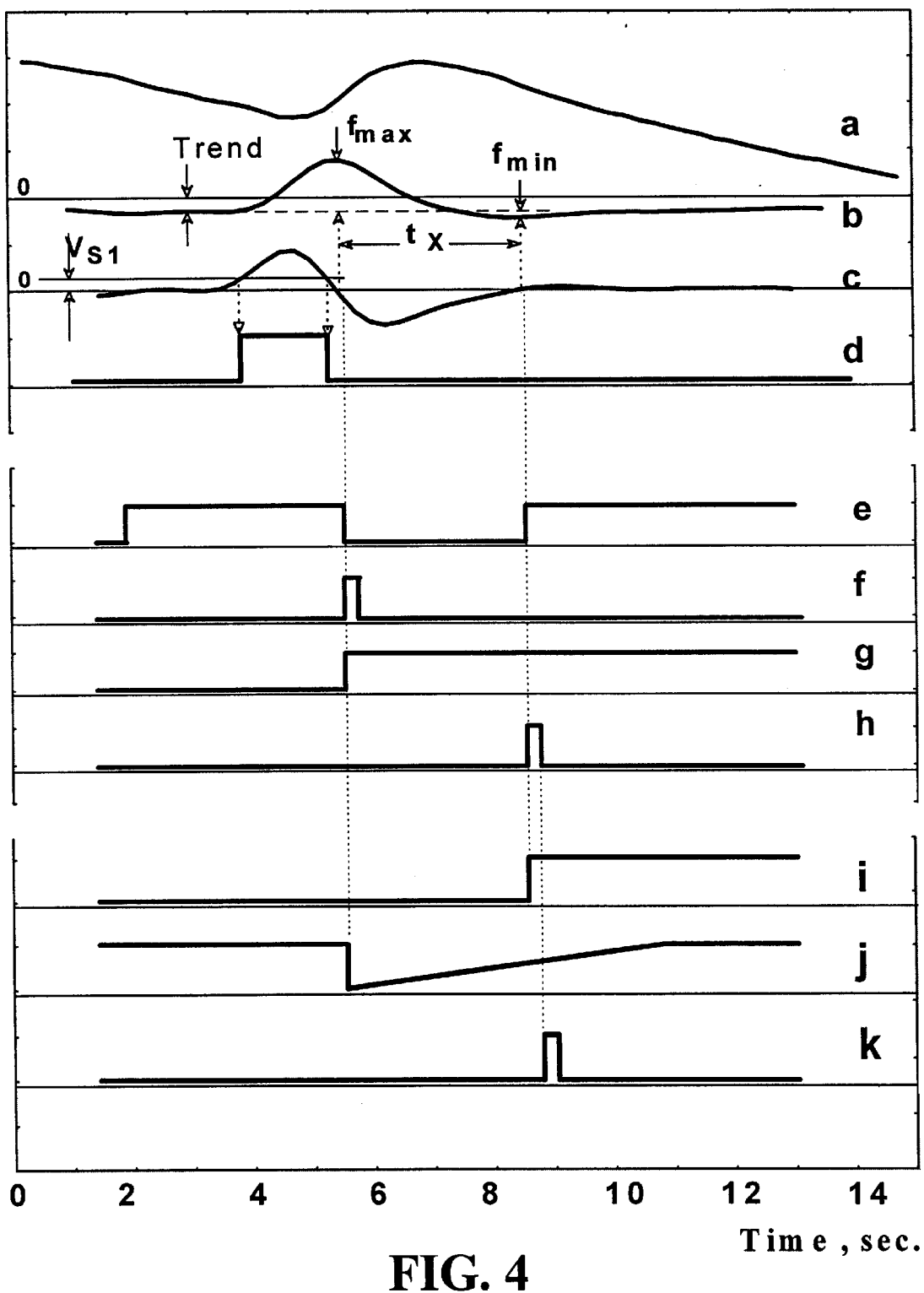
FIG. 4 shows waveforms explaining operation of the pulse shape analysis unit.

FIG. 3 shows an example of hardware implementation of the unit 12. In this variant the trend is determined by the averaged value of the first derivative over the time interval of 30 sec. FIG. 4 demonstrates the waveforms explaining operation of individual components of this unit.

The unit 12 has three inputs, vis. 11, 13 and 15. The input 11 to which the second derivative U" signal comes, is the signal input of two comparators 17 and 18, the reference input of the latter being fed with the zero potential. The inputs 13 and 15 are the inputs of the differential amplifier 19, the output of which is connected to signal inputs of sampling/storage circuits 20 and 21. The outputs of comparators 17, 18 are connected to the inputs of the synchronization unit 22, to inputs 23 and 24, respectively. The output 25 of the unit 22 is connected to the clock input of the sampling/storage circuit 20 and to the triggering input of the sawtooth generator 26. The output 27 is connected to the clock input of the sampling/storage circuit 21. The outputs of the sampling/storage circuits 20, 21 and of the sawtooth generator 26 are connected to the inputs of the comparator circuits 29, 30 and 31. Besides, the outputs of the circuits 20 and 21 are connected to the inputs of the analog divider 32, the output of which is connected to the input of the comparator circuit 33. The outputs of the circuits 29, 30, 31, 33 are connected to logic inputs of the "AND" circuit 34, vis. 35, 36, 37, 38. Besides, the output 28 of the synchronization circuit 22 is connected to the gate input 39 of the "AND" circuit 34. The comparator 17 has the reference voltage input $V_{S1}$ setting the threshold value for the second derivative exceeding of which triggers the analysis of the pulse shape. The reference inputs of the comparator circuits 29, 30, 31, 33 are connected to reference voltage sources (not shown in the figure) which determine the allowable limits for the selected parameters. Indexes in the equation symbols of these voltages ($V_{T1}$, $V_{T2}$; $V_{M1}$, $V_{M2}$; $V_{R1}$, $V_{R2}$; $V_{M3}$, $V_{M4}$) correspond to the abovementioned limits, within which the values of the characteristic parameters of the pulse shape (see inequalities (*)) should be confined. Should this be the case, a short logic "1" pulse is generated at the output 40 of the circuit 34.

Operation of the pulse shape analysis unit 12 shown in FIG. 3, is explained by the diagrams of FIG. 4. The diagram a) shows the example of a single pulse at the output of the logarithmic amplifier 7. To the input of the unit 12 the following signals are fed: the first derivative signal to the input 13 (diagram b), the first derivative signal averaged over 30 s to the input 15, and the second derivative signal to the input 11 (diagram c). The averaging time is chosen the least corresponding to the frequency range of EDA tonic component. This results in the voltage at the output of the differential amplifier 19 of the value U' corresponding to the first derivative of the input signal logarithm compensated for the trend. The value of U' is the relative value of voltage increment per one second expressed in % with respect to the value of the trend (see FIG. 4, b). It is this signal that is analyzed by the remaining part of the circuit. Timing of unit 12 components is carried out by the synchronization circuit 22 as follows. The signal from the output of the comparator 17 is a positive voltage step arising at voltage from the differentiating circuit 10 output exceeding the threshold value $V_{S1}$ (FIG. 4, c). The numerical value of a threshold voltage $V_{S1}$ in volts is selected so that it corresponds to second derivative variation by at least 0.2%, which has been determined experimentally. This positive voltage step (FIG. 4, d) is the triggering gate for the synchronization circuit 22. The comparator 18 (see FIG. 4, e) develops positive and negative voltage steps at its output in case of input signal U" crossing the zero line. After synchronization circuit triggering by the gate pulse from the comparator 17, short gate pulses are generated at each edge of the comparator 18 signal. The first gate is fed to the output 25 (FIG. 4, f) and is further fed to the sampling/storage unit 20 which registers the value of U' at the maximum (FIG. 4, g). The second gate (FIG. 4, h) is fed from the output 27 of the synchronization circuit 22 to the gate input of the second sampling/storage unit 21 which registers the value of U' at the minimum (FIG. 4, i). The first pulse is also fed to the input of the sawtooth generator 26, which, on arrival of the gate, produces the linearly increasing voltage (FIG. 4, j). The signal from the output of the sawtooth generator 26 is fed to the input of the comparator circuit 29. The output signal from the circuit 20 is fed to the comparator circuit input 30. The signal from the circuit 21 output is fed to the circuit 31. Besides, the signals from the outputs of the circuits 20, 21 are fed to inputs "A" and "B" of the analog divider 32. The signal from analog divider 32 output proportional to the ratio of input voltages $U_A/U_B$, is fed to the input of the comparator circuit 33. The signals from outputs of all comparator circuits 29, 30, 31 and 33 are fed to inputs 35, 36, 37, 38 of logic "AND" circuits 34 which is timed by the gate (see FIG. 4, k) fed to the gate input 39 from the output 28 of the circuit 22. As the result, a logic "1" pulse is formed at the output 40 of the circuit 34 provided all four inputs 35–38 are fed with the logic "1" signal at the moment of arrival of the gate to the input 39, the positive edge of which positive corresponds to the negative edge at the output 28.

The comparator circuits (29–31, 33) can be embodied by any of the traditional methods. They produce a logic "1" signal provided that the input voltage is confined in a range set by two reference voltages.

Figure 5:
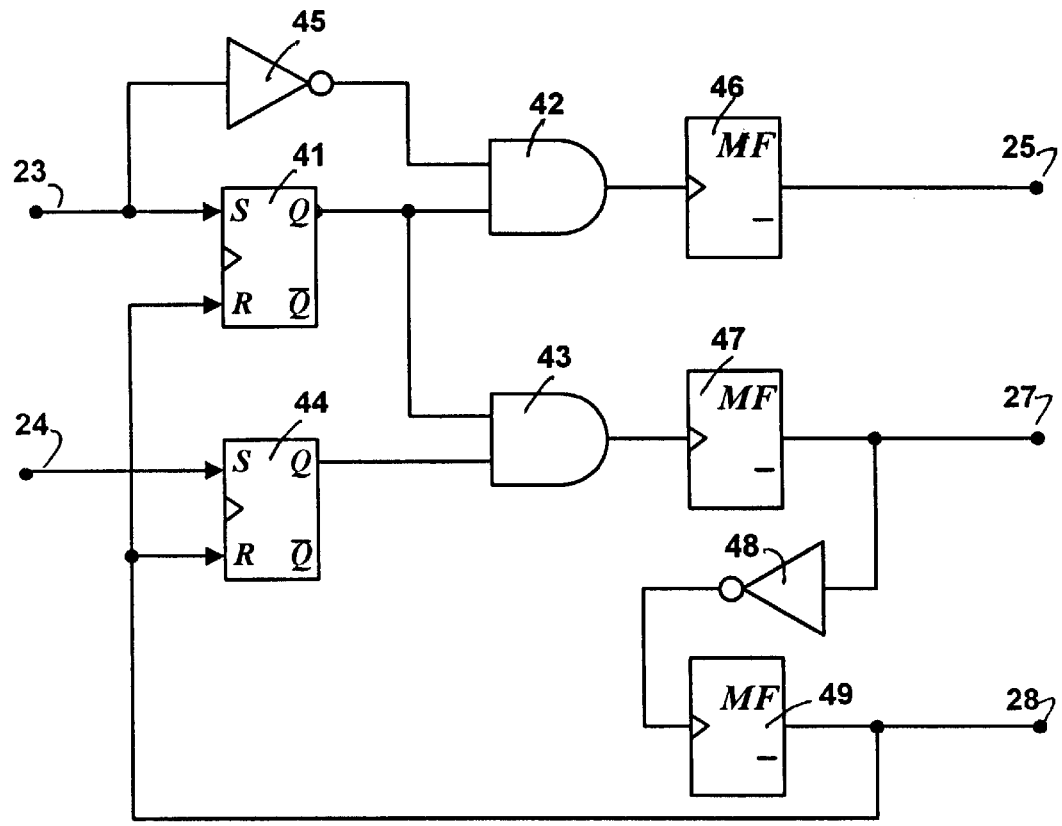
FIG. 5 shows the example of implementation of the synchronization unit incorporated into pulse shape analysis unit.

All internal gate signals are provided by the synchronization circuit 22, which can be embodied, for example, as follows (see FIG. 5). The circuit 22 has two inputs: 23 and 24. The input 23 is connected to the S-input of the RS-flip-flop 41 which is set to the "1" status by the positive edge from the comparator 17 (FIG. 4, d), i.e. at exceeding of the threshold level by the second derivative U" value. The output Q of the flip-flop 41 is connected to the inputs of the logic "AND" circuits 42 and 43, clearing passage for signals from the flip-flop 44 and the inverter 45 through these circuits. To the input 24, the signal from the comparator 18 (FIG. 4, e) is fed. The negative signal step from the input 24 is inverted by the inverter 45 and through the circuit 42 arrives to another monostable 46 which produced a gate pulse at the output 25 (see FIG. 4, h). The positive signal step from the input 24 sets the flip-flop 44 to the "1" state, which in its turn triggers the monostable 47 which produces a short positive pulse. This gate pulse is fed to the output 27 of the synchronization circuit (FIG. 4, f). The same pulse is fed to the input of the inverter 48, the output of which is connected to the input of the monostable 49. Thus, the circuit 49 is triggered by the trailing edge of the pulse from the output 47 and produces the third short gate pulse (see FIG. 4, k). This pulse is fed to the output 28 and is also used to reset RS-flip-flops 41 and 44, for which purpose it is fed to their "R"—inputs. After passage of this pulse the synchronization circuit 22 is again ready for operation until arrival of the next signal to the input 23.

As the result of the described operation of the synchronization circuit 22, a short logic "1" pulse is produced at the output 40 of the shape analysis unit 12 (see FIG. 3), provided the analyzed parameters are confined within the preset limits. One should note that in FIG. 2,d the labels S$_1$ and S$_2$ denote these very pulses; for visualization purposes they are superimposed on the plots of the first and the second derivatives of the analyzed signal.

Described above is the hardware implementation of the GSR signals discrimination.

At the same time, the discrimination of the desired GSR signal (EDA phasic component) from the background of noise and artifacts of movement can be carried out through software.

Figure 6:
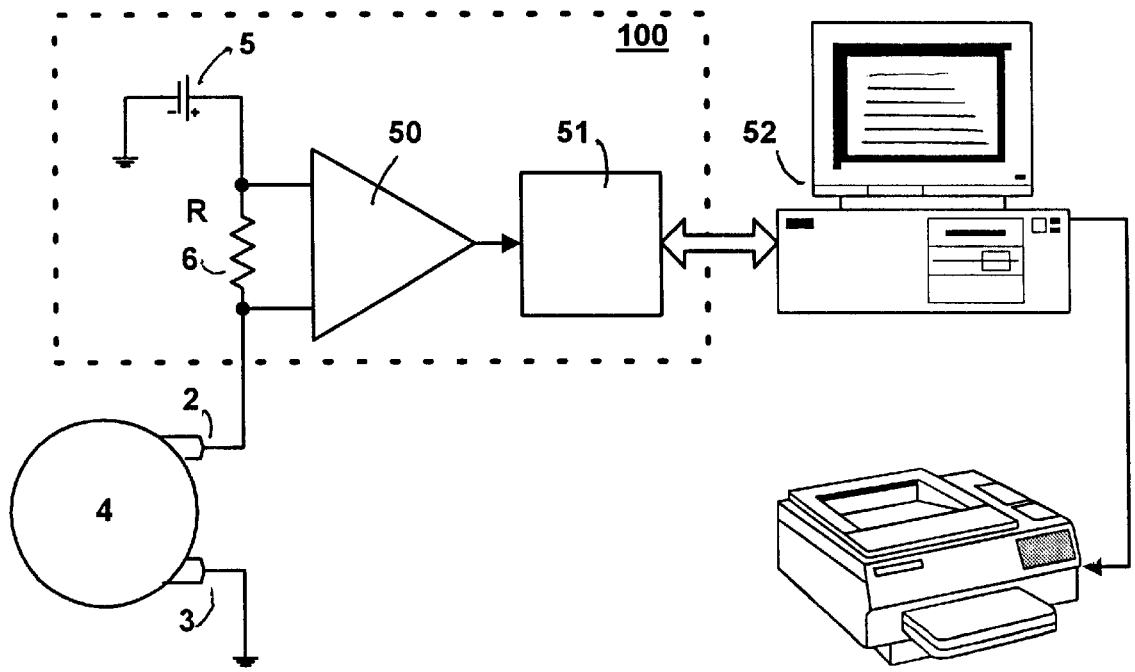
FIG. 6 shows the example of computer-based implementation of the device employing digital processing of the signal.

FIG. 6 shows the example of computer-based implementation of the device employing digital processing of the signal. The device includes the input unit 100 connected to the electrodes 2, 3 for imposing onto the skin of a subject 4, and the computer 52. The electrodes are connected through the resistor R (6) to the stabilized source 5 of the dc electric voltage. The signal from the resistor 6 is fed to the operational amplifier 50 with high input impedance and low output impedance said amplifier working in a linear mode. From the output of the amplifier 50 the signal is fed to the input of the standard 16-digit analog-to-digital converter 51 installed in the expansion slot of the IBM-compatible computer 52. Taking of logarithm and all subsequent analysis of the signal are performed digitally.

Using the values of current flowing between electrodes (I$_{meas}$), converted by the analog-to-digital converter, the first and second derivatives of the value 100·ln (I$_{meas}$) are calculated. In calculation of the first derivative correction for the trend is required. The trend value is defined as the average value of first derivative over the period 30 to 120 s.

Next the verification of the analyzed pulse belonging to GSR signals (verification of holding the inequalities (*)) is carried out. Should the shape parameters correspond to the preset criteria, said pulse is classified as a GSR pulse, in case of lack of such correspondence it is put down as an artifact.

As a result, the claimed method of GSR monitoring and the two versions of the device for its implementation enable to eliminate the interference brought about by artifacts the subject's movements, as well as the interference caused by non-biological factors increasing thereby the validity and reliability of the measurements.

The described method and devices can be used in various medical and psychophysiological researches where one of measured parameters is the skin electrical conductivity. These are, for example: training devices with skin resistance feedback for development of skills of relaxation and concentration of attention; system of professional selection, etc. Besides, the claimed invention can be applied, for example, for assessment of alertness level of a vehicle driver in real conditions featured by presence of numerous interferences.

The implementation of the devices can be easily carried out with a standard component base. The signal digital processing device version can be implemented on the basis of any personal computer, as well as employing any microcontroller or one-chip microcomputer. Communication of the measuring part and signal processing devices (both analog and digital) can be carried out by any of the known methods, both wire and wireless, for example, using a radiochannel or IR-channel.

While but one method and two devices under the invention have been shown and described, it will be apparent that numerous changes and modifications may be made therein. It is, therefore, to be understood that it is not intended to limit the invention to the examples shown, but only by the scope of the claims which follow:

What is claimed is:

1. A method of galvanic skin reactions monitoring comprising the operations:

fastening of two electrodes on the body of a subject, application of electric voltage to the said electrodes, monitoring time variations of electric current flowing between said electrodes, registering electric current pulses in the frequency band of an electrodermal activity phasic component, and analysis of the shape of each of said pulses, wherein:

(a) the signal is registered as the time derivative of the logarithm of electric current numerical value, (b) the trend value is defined, said trend value being caused by signal variations in the frequency band of electrodermal activity tonic component, and adjustment of the first derivative value is performed by subtracting the value of the trend from the said first derivative value, (c) the second derivative in time of said numerical value of the logarithm of the electric current is registered, (d) the pulse onset of said signal is determined as the moment of said second derivative exceeding a threshold value, and (e) conformity of the pulse shape to the preset criteria is determined, said pulse being classified as a phasic component pulse provided existence of this conformity and as an artifact otherwise.

2. A method according to claim 1, wherein the trend value (b) is determined as an average value of the first derivative over an interval of time, basically, 30 to 120 seconds.

3. A method according to claim 2, wherein the time of arrival of said first derivative pulse is determined as the moment of the second derivative (c) exceeding the threshold value by at least by 0.2%.

4. A method according to claim 1, wherein the trend value (b) is determined as an average value of the first derivative over an interval of time of 1–2 seconds, provided that values of the first and the second derivative during this interval of time are less than preset threshold values.

5. A method according to claim 4, wherein the time of arrival of said first derivative pulse is determined as the moment of the second derivative (c) exceeding the threshold value by at least by 0.2%.

6. A method according to claim 1, wherein the time of arrival of said first derivative pulse is determined as the moment of the second derivative (c) exceeding the threshold value by at least by 0.2%.

7. A method according to claim 1, wherein in determining the pulse shape, registered are the maximum (f$_{MAX}$) and the minimum (f$_{MIN}$) values of the first derivative minus the trend value (b), their ratio (r), the interval of time (t$_x$) between the minimum and the maximum of the first derivative, the moments of achievement by the first derivative of the maximum and the minimum values being determined as the moments of change of sign of the second derivative (c).

8. A method according to claim 7, wherein said preset criteria (e) of the analyzed pulse belonging to phasic component of EDA are determined as the following inequalities:

$$0.5 < f_{MAX} < 10$$

$$-2 < f_{MIN} < -0.1$$

$$1.8 < t_x < 7$$

$$1.5 < r < 10.$$

9. A device for monitoring of galvanic skin reactions comprising:

(a) an input unit connected to a plurality of electrodes and including a means of fastening said electrodes to a subject's skin, (b) means for suppression of pulse interference, (c) means for signal discrimination in the frequency band of an electrodermal activity phasic component, (d) means for phasic component pulses detection, and (e) a monitoring unit having at least one input, wherein the improvement consists in the assembly comprising the means for signal discrimination in the frequency band of electrodermal activity phasic component (c), and the means for phasic component pulses detection (d) being embodied as the assembly comprising:

(f) a unit for conversion of the logarithm of the input signal into the first and the second time derivatives, and (g) a pulse shape analysis unit, wherein the said means for suppression of pulse interference (b), the unit (f) for conversion of the logarithm of the input signal into the first and the second derivatives, and the pulse shape analysis unit (g) are connected serially to the input unit (a), the output of the pulse shape analysis unit (g) being connected to the input of the monitoring unit (e).

10. A device according to claim 9, wherein the assembly of the means for suppression of pulse interference (b), the means for signal discrimination in the frequency band of electrodermal activity phasic component (c), and the means for said component pulses detection (d) is embodied as the assembly comprising:

(f) a unit for conversion of the logarithm of the input signal into the first and the second time derivatives, (g) a pulse shape analysis unit, and (i) a low pass filter, wherein said lowpass filter (i), the unit (f) for conversion of the logarithm of the input signal into the first and the second time derivatives, and the pulse shape analysis unit (g) are connected serially to the input unit (a), the output of the pulse shape analysis unit (g) being connected to the input of the monitoring unit (e).

11. A device according to claim 9, wherein the input unit (a) is a stabilized source of electric voltage and a resistor connected serially to the electrodes, a logarithmic amplifier with a differential input stage, said resistor shunting the inputs of the said logarithmic amplifier.

12. A device according to claim 9, where in the unit for conversion of the logarithm of the input signal into the first and the second time derivatives (f) is embodied as a first differentiator (j) and a second differentiator (k) and a second lowpass filter (l), the output of the first differentiator (j) being connected to inputs of the second differentiator (k) and of the second lowpass filter (l), the outputs of which are the outputs of the unit (f) for conversion of the logarithm of the input signal into the first and the second time derivatives.

13. A device according to claim 9, wherein the unit for pulse shape analysis (g) further comprises:

(m) means for determining of the maximum variation rate of the signal at leading and trailing edges of the pulse being analyzed, (n) means for determining of its shape asymmetry, (o) means for determining of the pulse width, and (p) means for comparison of said values with the preset limits for generation of a signal indicating belonging of the pulse being analyzed to electrodermal activity phasic component.

14. A device for monitoring of galvanic skin reactions comprising:

(a) an input unit with electrodes connected to it and with a means of their fastenings to a subject's skin, (b) means for suppression of pulse interference, (c) means for signal discrimination in the frequency band of electrodermal activity phasic component, (d) means for phasic component pulses detection, and (e) a monitoring unit, wherein the improvement consists in the input unit (a) being a stabilized source of dc electric voltage and a resistor connected serially to the electrodes, an amplifier with a differential input stage, said resistor shunting the inputs of the said amplifier, and the output of said amplifier being connected to the input of an analog-to-digital converter (q) the digital output of which is the output of the unit (a); with this, the means (b), (c), (d), (e) are implemented as a program executed by a computer (r), the digital input of which is connected to the output of the input unit (a).

* * * * *